(12) United States Patent
Schauer

(10) Patent No.: US 8,649,017 B2
(45) Date of Patent: Feb. 11, 2014

(54) METHODS AND APPARATUS FOR SENSING A SUBSTRATE IN A CHAMBER

(75) Inventor: Ronald Vern Schauer, Gilroy, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 13/572,596

(22) Filed: Aug. 10, 2012

(65) Prior Publication Data
US 2013/0044326 A1 Feb. 21, 2013

Related U.S. Application Data

(60) Provisional application No. 61/524,090, filed on Aug. 16, 2011.

(51) Int. Cl.
*G01N 21/55* (2006.01)

(52) U.S. Cl.
USPC ............................................ 356/445

(58) Field of Classification Search
USPC ............................................ 356/445
See application file for complete search history.

(56) References Cited

U.S. PATENT DOCUMENTS

| | | | |
|---|---|---|---|
| 5,563,798 A | 10/1996 | Berken et al. | |
| 6,313,596 B1 | 11/2001 | Wyka et al. | |
| 6,592,673 B2 | 7/2003 | Welch et al. | |
| 6,630,996 B2 * | 10/2003 | Rao et al. | 356/237.5 |
| 8,057,602 B2 | 11/2011 | Koelmel et al. | |
| 2004/0253824 A1 * | 12/2004 | Tegeder | 438/696 |
| 2006/0124873 A1 | 6/2006 | Anza | |
| 2007/0232009 A1 | 10/2007 | Schulz | |
| 2008/0077271 A1 | 3/2008 | Sundar | |

OTHER PUBLICATIONS

International Search Report and Written Opinion of International Patent Application No. PCT/US12/050475 mailed Feb. 1, 2013.

* cited by examiner

*Primary Examiner* — Tu Nguyen
(74) *Attorney, Agent, or Firm* — Dugan & Dugan, PC

(57) ABSTRACT

The present invention provides methods, apparatus, and systems of sensing a substrate in a chamber. The invention includes emitting radiation of at least two different wavelengths; directing the emitted radiation of a first wavelength through a view port of a chamber at an interior of the chamber; directing the emitted radiation of a second wavelength through the view port of the chamber at a location of a hole in a blade of a substrate carrier; detecting any of the emitted radiation reflected by the blade, the interior of the chamber, or a substrate on the blade; and determining if a substrate is present on the blade based on the reflected radiation detected. Numerous additional aspects are disclosed.

20 Claims, 18 Drawing Sheets

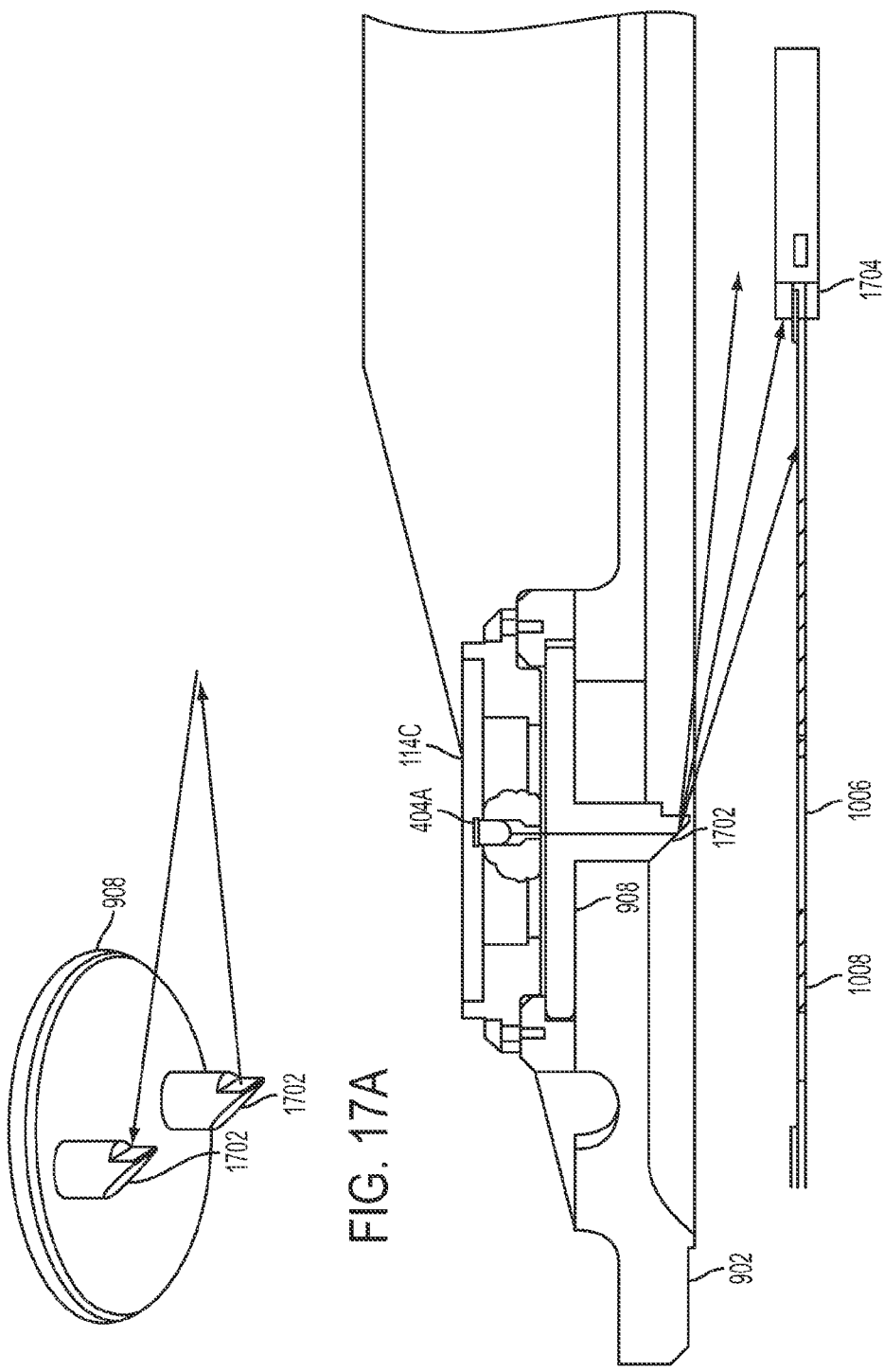

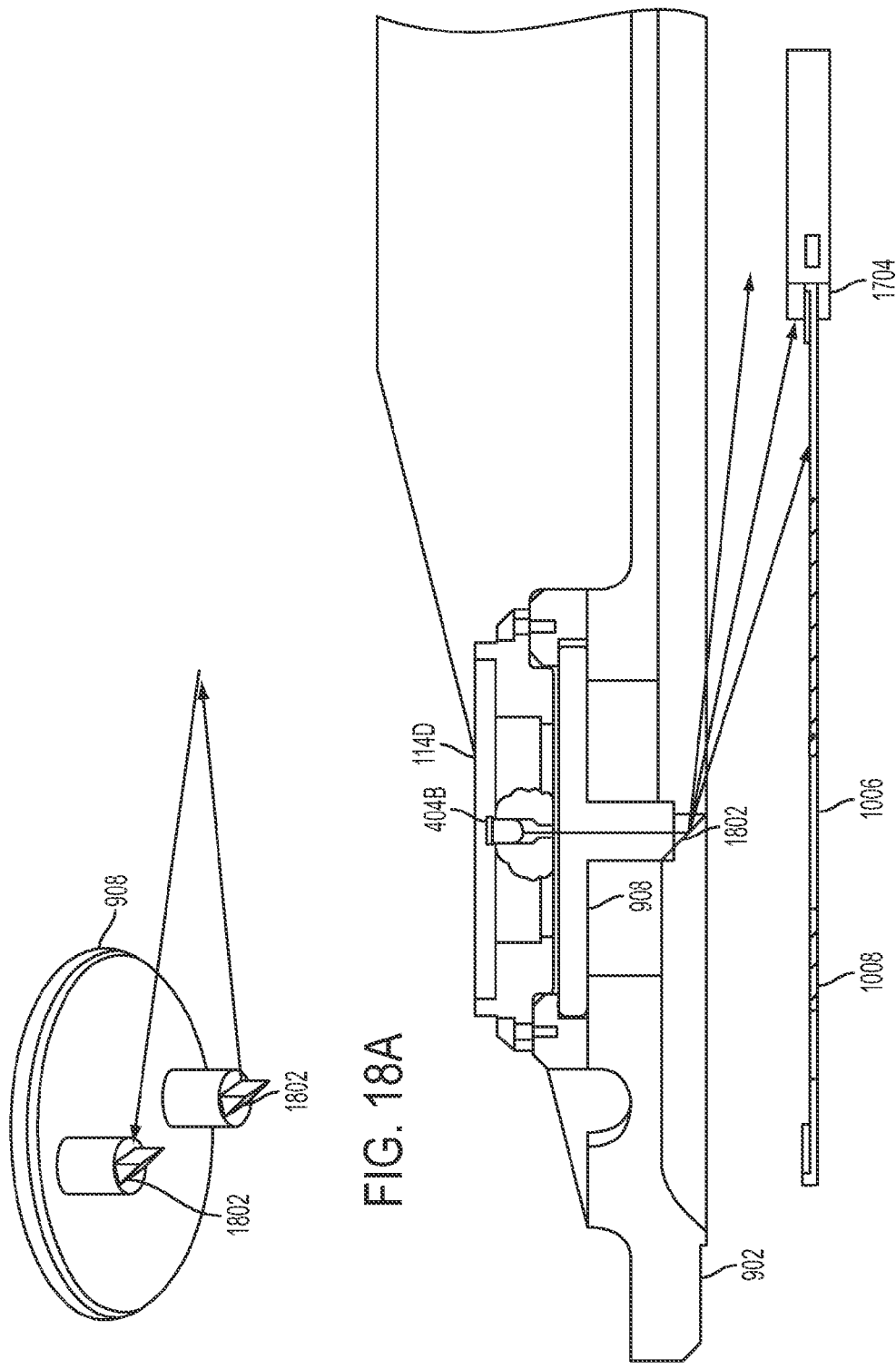

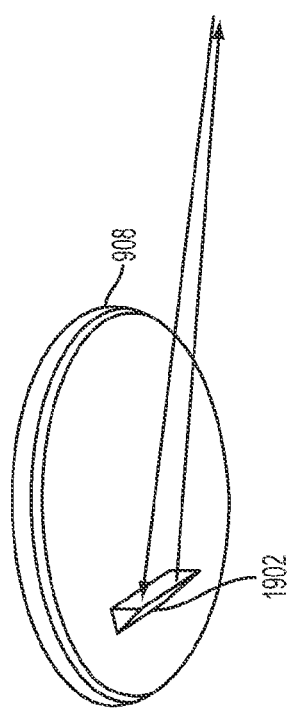
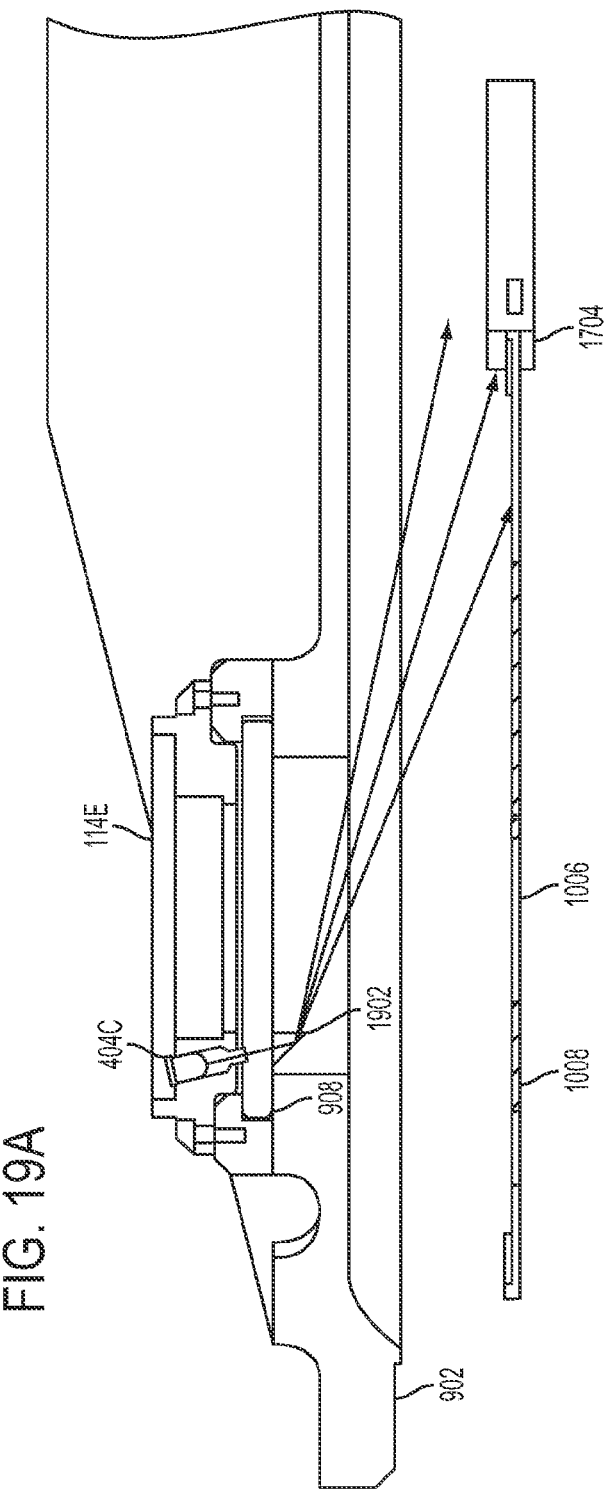

METHODS AND APPARATUS FOR SENSING A SUBSTRATE IN A CHAMBER

RELATED APPLICATIONS

The present application claims priority from U.S. Provisional Patent Application Ser. No. 61/524,090, filed Aug. 16, 2011, entitled "METHODS AND APPARATUS FOR SENSING A SUBSTRATE IN A CHAMBER" which is hereby incorporated herein by reference in its entirety for all purposes.

FIELD

The present invention is directed towards methods and apparatus for sensing a substrate in chamber. More particularly, the present invention is directed towards methods and apparatus for sensing different substrates, each potentially having a different reflectivity.

BACKGROUND

Due to the differing reflectivity of substrates, it may be difficult to reliably optically detect a substrate in an electronic device processing chamber using conventional optical sensors. Thus, what are needed are reliable methods and apparatus for sensing different substrates in a chamber, where each substrate potentially has a different reflectivity.

SUMMARY

The embodiments of the present invention generally relate to methods and apparatus for sensing a substrate.

In some embodiments, the present invention provides a method of sensing a substrate in a chamber. The method includes emitting radiation of at least two different wavelengths; directing the emitted radiation of a first wavelength through a view port of a chamber at an interior of the chamber; directing the emitted radiation of a second wavelength through the view port of the chamber at a location of a hole in a blade of a substrate carrier; detecting any of the emitted radiation reflected by the blade, the interior of the chamber, or a substrate on the blade; and determining if a substrate is present on the blade based on the reflected radiation detected.

In some other embodiments, the present invention provides an apparatus for sensing a substrate in a chamber. The apparatus includes a plurality of emitters for emitting radiation of at least two different wavelengths; a member for directing the emitted radiation of a first wavelength through a view port of a chamber at an interior of the chamber; one or more apertures in the member for directing the emitted radiation of a second wavelength through the view port of the chamber at a location of a hole in a blade of a substrate carrier; one or more sensors for detecting any of the emitted radiation reflected by the blade, the interior of the chamber, or a substrate on the blade; and logic coupled to the sensors and adapted to determine if a substrate is present on the blade based on the reflected radiation detected.

In yet other embodiments, the present invention provides an apparatus for sensing a substrate in an electronic device processing tool. The apparatus includes a mounting member adapted to couple the apparatus to a view port of the electronic device processing tool; a radiation source of a first wavelength disposed within the mounting member and adapted to illuminate an interior of the electronic device processing tool; a radiation source of a second wavelength disposed within the mounting member and directed to illuminate a location of a hole in a blade of a substrate carrier in the electronic device processing tool; one or more sensors disposed to receive radiation reflected from the substrate, the blade, and the interior of the electronic device processing tool; and logic coupled to the sensor and adapted to determine if a substrate is present on the blade based on the reflected radiation received.

These and other features and aspects of the present invention will become more fully apparent from the following detailed description of exemplary embodiments, the appended claims and the accompanying drawings.

BRIEF DESCRIPTION OF THE DRAWINGS

An artisan of ordinary skill will understand that the drawings, described below, are for illustration purposes only. The drawings are not intended to limit the scope of the present teachings in any way.

FIGS. 17A to 19B are three pairs of partial perspective drawings and cross-sectional drawings, respectively, depicting three alternative embodiments using side-looking optics for sensing a robot wrist according to some aspects of the present invention.

DETAILED DESCRIPTION

Figure 1:
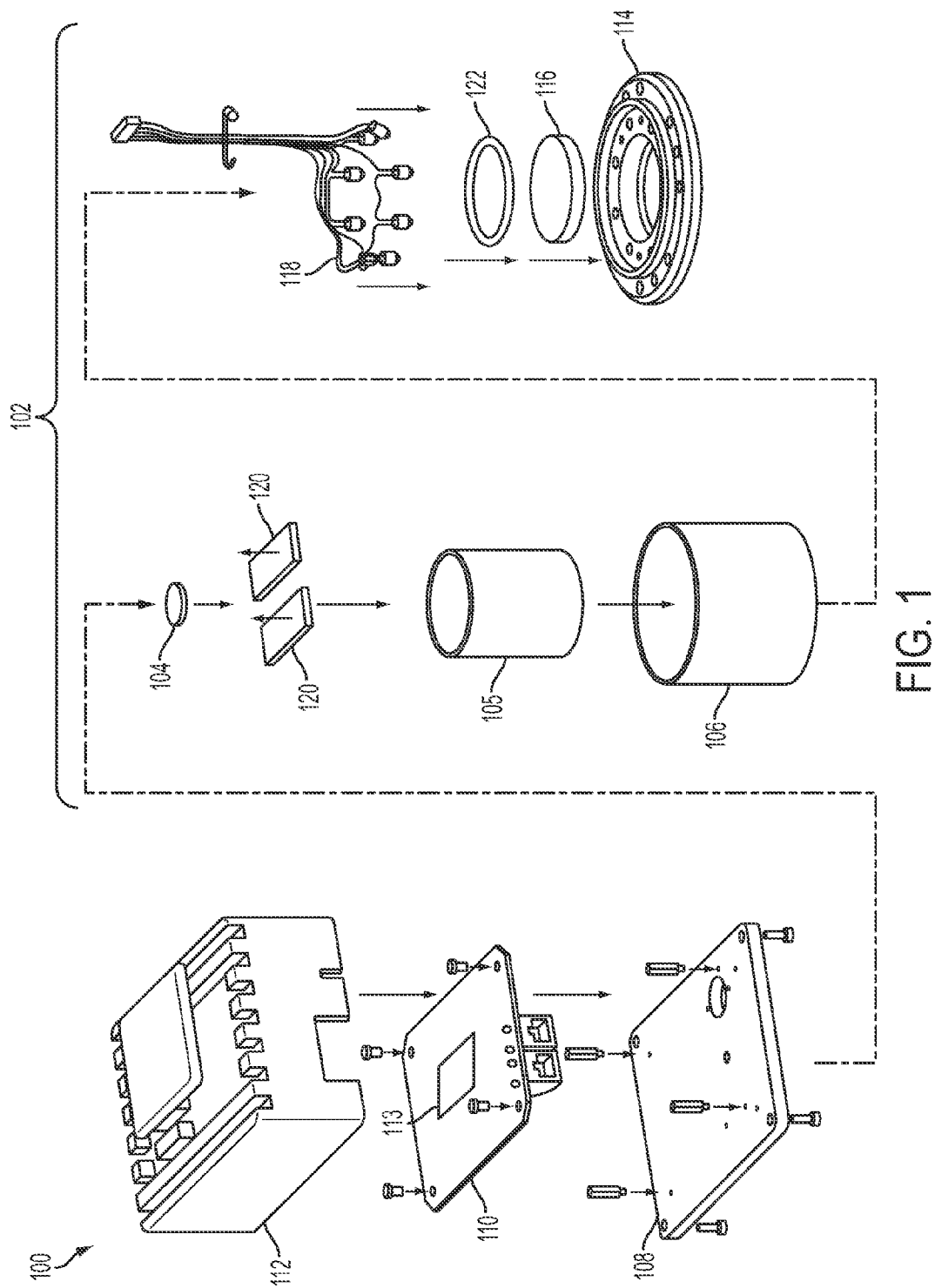
FIG. 1 depicts an exploded perspective view of an example apparatus embodiment of the present invention.

For the purpose of interpreting this specification, whenever appropriate, terms used in the singular will also include the plural and vice versa. The use of "or" is intended to mean "and/or" unless stated otherwise. The use of "a" herein is intended to mean "one or more" unless stated otherwise or where the use of "one or more" is clearly inappropriate. The use of "comprise," "comprises," "comprising," "include," "includes," "including," "has," and "having" are interchangeable and not intended to be limiting. Furthermore, where the description of one or more embodiments uses the term "comprising," those of ordinary skill in the art would understand that, in some specific instances, the embodiment or embodiments can be alternatively described using the language "consisting essentially of" and/or "consisting of."

While the present teachings are described in conjunction with various embodiments, it is not intended that the present teachings be limited to such embodiments. On the contrary, the present teachings encompass various alternatives, modifications, and equivalents, as will be appreciated by those of ordinary skill in the art.

The present invention provides systems, methods, and apparatus for sensing a substrate in a chamber. Using at least two different sets of emitters and detectors operating at two different wavelengths (or wavelength ranges), the present invention senses, in parallel, for two distinct conditions to determine if a substrate is present on a blade in a processing chamber. The first condition is whether radiation at a first wavelength directed into a chamber is reflected back at a level that is above or below the range that an empty blade used to support a substrate would reflect back radiation. If so, the system determines a substrate is present. The second condition is whether radiation at a second wavelength, and specifically directed at the location of a center hole in the blade, is reflected back at a level that is greater than the ambient level of the radiation of the second wavelength. If so, the system determines a substrate is present.

The first condition covers the cases in which a substrate is more or less reflective than a blade. Given that a blade has a range of reflectivity defined by an upper threshold and a lower threshold, the present invention includes logic adapted to determine that a substrate is present whenever the amount of radiation reflected is above the upper threshold and below the lower threshold. However, when a substrate has a reflectivity within the same range as an empty blade, the second condition is used to determine if a substrate is on the blade. The second condition specifically looks at the location of a hole in the substrate blade and logic adapted to determine if the radiation of the second wavelength is being directly reflected to determine if a substrate is present. The present invention is adapted to test both conditions concurrently but in other embodiments the determinations may be made sequentially.

In one or more embodiments, the substrate detection apparatus is provided with a unitary mounting member adapted to easily couple to viewing ports of one or more electronic device processing tools (e.g., transfer chambers, processing chambers, etc.), such as the Centura® or Endura® processing tools manufactured by Applied Materials Inc. of Santa Clara, Calif. The mounting member may be designed to prevent reflections off the window of a viewing port of the light (e.g., optical spectrum energy) used by the substrate detection apparatus, which otherwise may affect the substrate detection process. To reliably detect substrates that may include non-reflective materials, the substrate detection apparatus includes one or more radiation sources (e.g., optical spectrum energy sources) which may range from infrared (about 1500 nm) through far ultraviolet (about 150 nm), one or more optical detectors adapted to detect the wavelength or wavelengths that the radiation sources emit and/or secondary emissions from the substrate, one or more diffusers, and in some embodiments, one or more narrow-band filters adapted for sensitivity to the type of substrate being detected. The filter wavelengths may be different from the wavelengths emitted by the light sources since in some cases secondary or shifted emissions are reflected from the substrate. Selection of suitable filters may remove the need for special alignments. To assist in detection, the substrate detection apparatus may also include features that are adapted to block ambient light sources to reduce background signals. Additional devices to modify the optical path so as to reduce the effect of pattern geometry on substrates may also be included. Such devices may include but are not limited to, lenses, windows, collimators and diffusers. Automated (e.g., via control software) and/or manual mechanisms for controlling the intensity of energy emitted from the radiation sources and the gain of the detectors during operations may be provided in some embodiments.

The substrate detection apparatus also includes a number of features that improve safety and reliability. For example, in some embodiments, the substrate detection apparatus includes an enclosure having shielding designed to limit and/or prevent unintentional operator exposure to optical energy sources and to provide couplings in a manner that avoids disconnection of power when opening the enclosure. In one or more embodiments, the apparatus may include safety interlock switches that prevent unintentional exposure to optical energies outside the eye-safe wavelength range.

Stable radiation sources, such as solid state light sources that emit at a fixed wavelength may be used singly or in combination, as may be appropriate. Such sources may be chosen so as to provide long and stable service (e.g., up to 500 to 1000 times the service of light sources used in conventional film detection devices). The sources may be designed to turn on in an extremely short time, so that they can be energized only for the brief time required to take a measurement and make a determination (requiring no repeated calibrations), resulting in appreciable energy savings. The extremely rapid turn-on and brief use of the light sources promotes safety. For example, where ultra-violet or infrared sources are employed, exposure to which for certain periods may be hazardous, the light source is energized only for brief periods while other safety criteria (e.g., shielding, enclosure closed) are met.

The present invention also provides a control system and/or software adapted to interface with and control the substrate detection apparatus according to the invention. The control system may include one or more logic circuits adapted to: perform and record calibrations of the substrate detection apparatus; determine the presence or absence of a substrate; and couple to other control systems in a fabrication facility.

In some embodiments, the present invention may utilize a mounting means that is specific to commercially available (e.g., Applied Materials' Centura® and Endura®) transfer chamber lid viewing window ports (e.g., a simple bolt-on). This mounting means is conceived to be easily adaptable to other types and styles of equipment.

The present invention utilizes a mounting means that is easily adaptable to all types and styles of processing chamber view ports. The present invention is designed to block ambient light sources for sensing uniformity. This is an integral feature of the present invention that, unlike other methods, does not require additional engineering methods or solutions. Embodiments of the present invention limit or prevent unintentional operator exposure to the optical energy sources. Other features may include built-in safety cutoff switches (as necessary) and engineering safety solutions such as designing the connecting cabling in a manner that prevents enclosure opening without disconnection of power. Singly and in combination, these enhance operator and installer safety.

The present invention is designed as a compact unitary (modular) bolt-on assembly. This is in contrast to prior art systems that are assembled in place from various parts, integrated into various chamber components, and whose components may be scattered about the system.

The present invention is designed to electrically interface to, or readily be adapted to interface to, all substrate processing systems. This interface is designed to be very simple in nature so as to enhance flexibility. The present invention may, in some embodiments, also include an interactive and configurable system interface and use, for example, serial data transfer for communication with and/or control by a host system. However, the presence and use of such interfaces is optional and not required for operation.

Configuration of the present invention during manufacture is simple and highly tolerant of modest skill sets. The device is tuned to the desired wavelength band or bands using standard commercial narrow band optical filters and light source selections or by selection of light sources and sensors that are natively selective of specific wavelength bands.

Solid state light sources and/or other fixed wavelength energy sources may be used in combination as may be appropriate. These sources may be chosen for long and stable service (e.g., 500×-1000× the service life of prior art sources). As the present sources may not degrade significantly over their normal service lifetimes, they may be considered permanent.

In some embodiments, the radiation sources may be "instant on", requiring no appreciable warm up periods and are highly energy efficient. The instant on sources utilized by the present invention may provide a safety enhancement. Where ultra-violet or infrared sources are utilized, these sources may be optionally energized for brief periods of time and only if all safety interlock criteria are met.

According to the present invention, no special windows, fiber optics, vacuum seals or any other such items are required for installation and usage. The pre-existing vacuum seals of the chambers are not breached during installation or usage. This allows very rapid installation and service to be performed without changes to substrate fabrication processes or chambers.

The present invention may include an optical spectrum energy source or plurality of sources, which may range in wavelength from far infrared (~1500 nanometers) into ultra-violet (~150 nanometers) inclusive, as necessary for sensing reliability. In some embodiments, at least two separate wavelengths will be utilized, and in other embodiments, three or more may be used. In some embodiments, separate substrate presence radiation emitter and detector devices/level detection sensors (e.g., optical energy emitters and detectors/sensors) are used and operate at substantially differing wavelengths to avoid interference with one another.

Embodiments of the present invention may provide an automated or manual means to control the intensity of the optical energy sources during service operations and as part of an automated calibration sequence. Likewise, embodiments of the present invention may provide an automated or manual means to control the gain or sensitivity of the sensing device during service operations and as part of an automated calibration sequence.

The present invention may include an optical sensor or group of sensors capable of detecting the wavelength or wavelengths that the optical energy sources emit, and/or secondary emissions from the wafer being sensed. In addition the invention may include an optical sensor or group of sensors capable of detecting the background reflections from a robot blade when a wafer is not present. Embodiments include the mountings for said optical sensors, designed such that they may be easily reconfigured as necessary. The invention may include an optical path that limits the sensor or sensors to a certain area or range. Such a path may contain lenses, windows, collimators, diffusers, and other devices to enhance this function and also to help negate the effects of pattern geometry on the wafers being sensed.

Embodiments include means of interfacing between the optical sensor or sensors and the host equipment as well as a logic circuit capable of performing and recording calibrations of the assembly, both in production and in service conditions. The logic circuit that may be adapted to make decisions about the substrate being sensed based upon the calibrations including combinations of conditions sensed by multiple detectors operating at differing wavelengths.

The logic circuit that may also be adapted to determine the presence or absence of substrates in the field of view of the sensing device or devices, including instances where substrate blade face openings are not provided and where the wafer is sufficiently dark (non-reflective) as to defeat normal sensing schemes.

The present invention may also provide a mounting geometry that prevents first and second surface reflections from the vacuum chamber window from adversely affecting the returned sensing optical signals. In some embodiments, an optional integral reference target surface for self-calibration or a standardized target wafer to help effect said calibration may be provided. A mechanical array device to contain and align the optical energy sources and to direct their output to a convergent point and also for a controlled illumination field area may also be provided.

In additional embodiments of the invention, more than one wavelength of optical spectrum energy source (polychromatic aggregate source) may be used. One or more optical filters specified for sensitivity with the semiconductor substrate film type being detected or detector devices adapted for sensing specific wavelengths to the exclusion of others may be used. Note that the filter wavelengths may or may not be the same as the incorporated optical energy sources, because in some cases secondary or shifted emissions or combinations thereof are to be detected. The multiplicity of optical wavelengths in the energy source may be simultaneous, sequenced, or selectively enabled in different embodiments.

In other embodiments, a coaxial light source which is effected by means of beam splitters, multiple-strand fiber optics, mirrors, or similar means may be used. The coaxial light source may be present in lieu of a convergent light source or in addition to such a source having a different field of view or wavelength. In some embodiments, the coaxial light source may be present in conjunction with the convergent light source, and may be used separately, simultaneously, or in combination to effect measurements.

Turning to FIG. 1, a specific example embodiment of the present invention is now described for the purposes of illustration. An exploded perspective view of an example embodiment of a substrate detection apparatus 100 of the present invention is provided. The example apparatus 100 includes a base assembly 102 that includes an optional upper diffuser 104, a diffusing tube 105, and is surrounded by an outer tube housing 106. The outer tube housing 106 couples to a plate 108, which supports a sensor assembly 110 and is surrounded by a shield housing 112. The sensor assembly 110 may include logic 113 for controlling the apparatus 100. The base assembly 102 further includes a base mounting member 114 that is adapted to support both a lower diffuser 116 and a radiation source array 118, as well as to couple to a view port of a processing chamber as will be described in detail below.

As mentioned above, the base assembly 102 includes the inner diffusing tube 105. The inner diffusing tube 105 supports upper support members 120 which are adapted to hold the optional upper diffuser 104. A spacer 122 (e.g., an O-ring) may be disposed around the lower diffuser 116 to position the lower diffuser 116 within the base mounting member 114.

The apparatus 100 is adapted to easily be attached to a processing chamber (not shown in FIG. 1, but see FIG. 8) (e.g., a transfer chamber, a processing chamber, etc.) at a view port (not shown) of the processing chamber. When attached, the apparatus 100 is disposed to both illuminate and scan substrates within the processing tool through the view port. The lower portion of the optical base assembly 102 is shaped to fit within a frame (not shown) of the view port so that the bottom annular surface 202 (FIG. 2) of the assembly 102 sits flush with the transparent material (e.g., quartz window) of the view port and the outer flange edge 204 (FIG. 2) of the assembly 102 overhangs the frame of the view port to facilitate attachment (e.g., via machine bolts). In some embodiments, the structural components of the apparatus 100 (e.g., the housings, base plate, etc.) may be formed from aluminum or any other practicable material.

If present, the optional upper diffuser 104 may be made of opal glass which is translucent but not transparent to optical energy. Optional upper diffuser 104 may or may not be present depending upon the specific application, intensities, and/or wavelengths used. In some embodiments, a thin layer of opal glass (e.g., approximately 0.05 to approximately 0.3 mm thick and preferably approximately 0.1 mm thick) may be fused to a thicker clear piece of glass (e.g., approximately 6 mm thick) to form the optional upper diffuser 104. The optional upper diffuser 104 is disposed horizontally and in line with a central radiation path that extends up from the view port of the processing tool, through the center of the base assembly 102, through the optional upper diffuser 104, through an aperture in the base plate 108 (which may include one or more optical filters), and into the sensor assembly 110.

The outer tube housing 106 (along with the shield housing 112) is adapted to shield the base assembly 102 and to both prevent ambient light from entering the sensor assembly 110 as well as protect operators from exposure to radiation from the base assembly 102. Although the outer tube housing 106 is depicted as a tube, any practicable shape may be used.

The sensor assembly 110 is disposed above and supported by the plate 108. The sensor assembly 110 is adapted to generate a signal indicative of the detection of a particular target range of energy wavelengths in response to receiving radiation energy that is inclusive of the target range from the processing chamber. In some embodiments for example, a Model PM100-V detector assembly, commercially available from Verity Instruments, Inc. of Carrollton, Tex., may be used as the sensor assembly 110. In such embodiments, the sensor assembly 110 may be embodied as a replaceable or upgradeable modular component that is separate from the rest of the circuitry of the apparatus 100. In other embodiments, the sensor assembly 110 may be embodied as an integral component of a controller of the apparatus 100. In some embodiments, the plate 108 may also support an optical bandpass filter in or adjacent the aperture between the sensor assembly 110 and the optional upper diffuser 104. Additional and other types of filters, as discussed above, may be used.

The shield housing 112 covers the top of the apparatus 100 and encloses the sensor assembly 110 as well as the logic 113 and other circuitry of the apparatus 100. As with the outer tube housing 106, the shield housing 112 is adapted to prevent ambient light from entering the sensor assembly 110 as well protect operators from exposure to optical energy from the base assembly 102.

Figure 2:
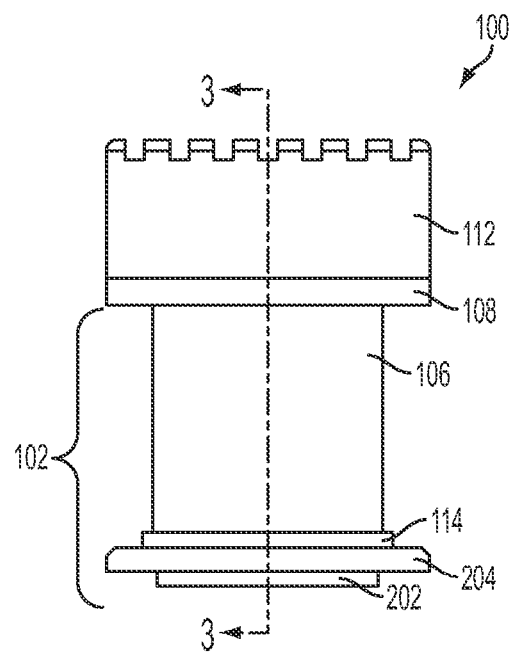
FIG. 2 depicts a side view of the example apparatus embodiment of FIG. 1.

Turning to FIG. 2, a side view of the apparatus 100 is depicted that illustrates how the various components shown in FIG. 1 fit together. Note that several fasteners are omitted from both FIGS. 1 and 2 for clarity. As indicated above, the lower annular surface 202 of the apparatus 100 is adapted to sit flush with the window surface of a processing chamber view port. Also as indicated above, the outer flange edge 204 of the assembly 102 is adapted overhang the frame of the view port to facilitate attachment. The outer flange edge 204 includes holes to allow the assembly to be securely but removeably attached to the processing tool (e.g., via bolts).

Figure 3:
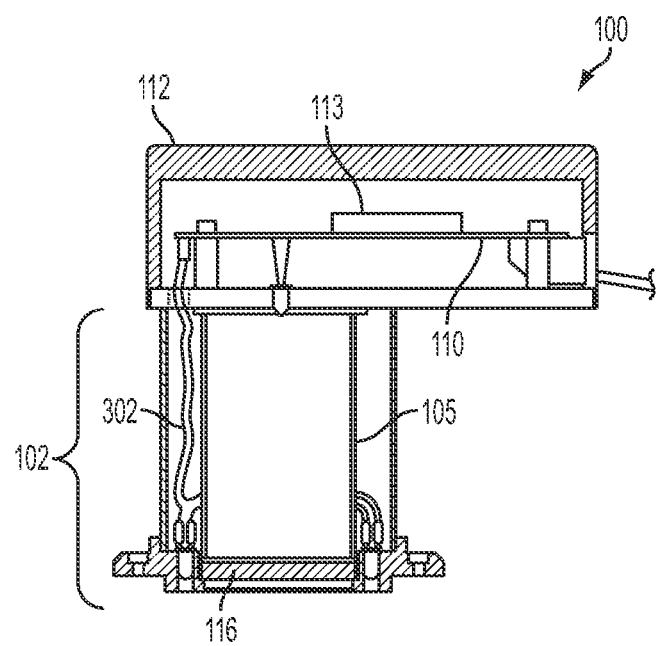
FIG. 3 depicts a cross-sectional view of the example apparatus embodiment of FIG. 2 taken along line 3-3.

Turning to FIG. 3, a cross-sectional view of the example apparatus 100 is depicted. The cross-section is taken along the line identified as 3-3 in FIG. 2. Note that the elements described above with respect to FIGS. 1 and 2 are labeled using the same reference numerals as in FIGS. 1 and 2. In FIG. 3 internal components of the base assembly 102 and the apparatus 100 are depicted in their assembled positions. Specifically, the lower diffuser 116 is shown disposed within the inner diffusing tube 105. In addition, the logic 113 (e.g., a programmable controller) is depicted on the sensor assembly 110. The logic 113 may be coupled to the optical sensor assembly 110 via circuit board lines and to the radiation source array 118 via cabling 302 of the array 118.

As with the optional upper diffuser 104 (not shown in FIG. 3), the lower diffuser 116 may be made of opal glass. In some embodiments, a thin layer of opal glass (e.g., approximately 0.05 mm to approximately 0.3 mm thick and preferably approximately 0.1 mm thick) may be fused to a thicker clear piece of glass (e.g., approximately 6 mm thick) to form the lower diffuser 116. In some embodiments, lower diffuser 116 may be disposed so that the opal glass layer is on the top surface of the lower diffuser 116, effectively further recessing the diffuser 116 into the inner diffusing tube 105.

The inner diffusing tube 105 may be formed from aluminum and includes an inner surface coated with a randomly textured material to further scatter and randomize radiation energy traveling through the tube 105. In some embodiments, the inner surface of the inner diffusing tube 105 may be anodized to form a rough oxide layer. The thickness of the anodized layer may be between approximately 20 to 40 microinches RMS, and preferably approximately 32 microinches RMS.

The logic 113 may include a processor, logic circuitry, and/or any combination of hardware and software that is adapted to use the apparatus 100 to execute the methods of the present invention. For example, the logic 113 may include program code that is adapted to activate the supply base assembly 102 to illuminate a substrate in a processing tool in response to receiving a signal indicating detection should begin (e.g., a substrate is expected to be present). In some embodiments, the logic 113 may include program code that is adapted to use the base assembly 102 to detect the presence of a substrate in the processing chamber in accordance with the methods detailed below with respect to FIGS. 13 and 14. In some embodiments, the logic 113 may include program code that is adapted to send a signal to a host system or process tool controller indicating that a substrate is present or not present based upon receiving one or more signals from the sensor assembly 110 indicating the detection of a certain wavelength of radiation energy received reflected from the substrate. In some embodiments, the logic 113 may include program code that is adapted to calibrate the apparatus 100, to control the intensity of the radiation energy sources, and/or to adjust the gain of the sensors in the sensor assembly 110. The logic 113 may also include interface ports, memory, clocks, power supplies, and other components to support operation of the logic 113.

Figure 4:
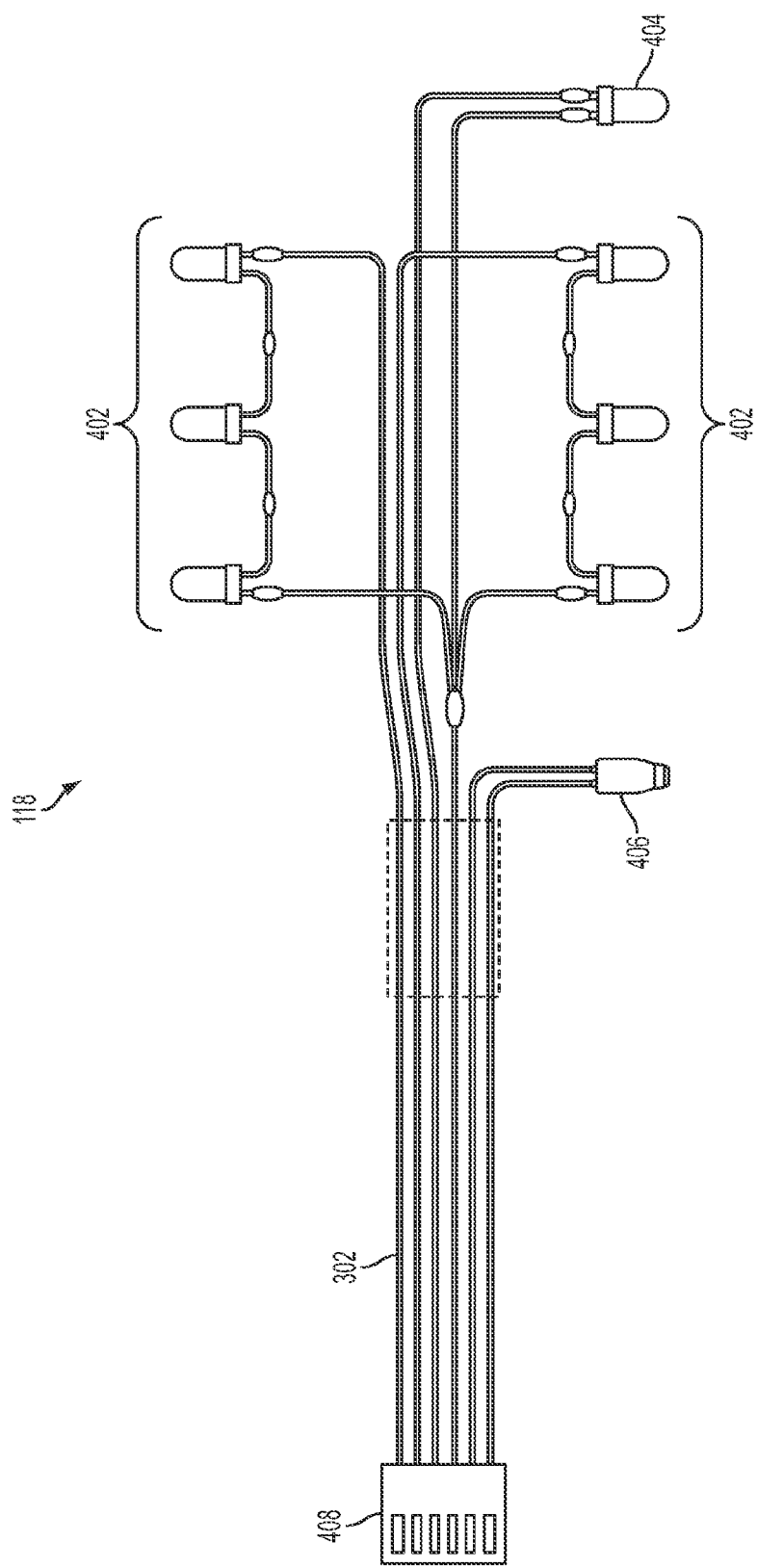
FIG. 4 depicts a detail view of an example embodiment of a component of FIG. 1.

Turning to FIG. 4, a diagram depicting the radiation source array 118 is provided. The example array 118 shown includes six LEDs used as radiation sources 402. However, any type and number of practicable radiation sources 402 may be used with a corresponding number of apertures in the base mounting member 114. As indicated above, various different types of sources may be used to generate radiation energy, for example, in the optical spectrum range from infrared (about 1500 nm) through far ultraviolet (about 150 nm).

Figure 5:
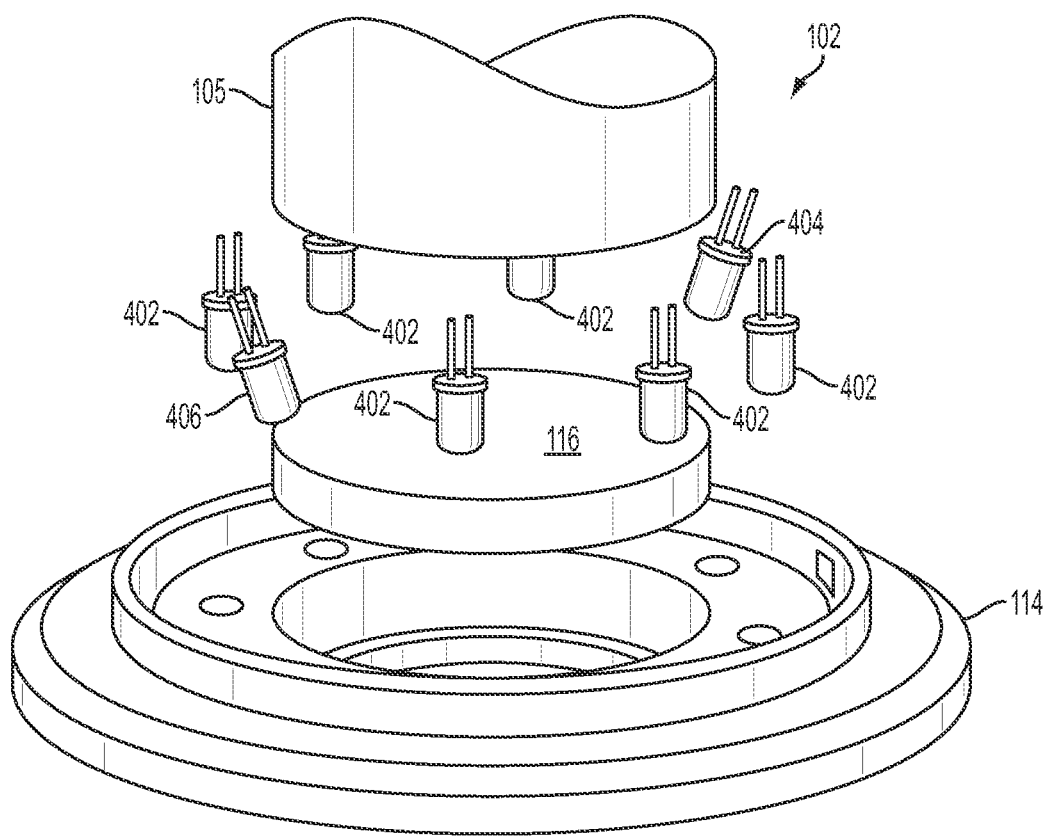
FIG. 5 depicts an exploded detailed perspective view of a portion of the example apparatus embodiment of FIG. 1.

In embodiments of the invention as shown in FIG. 5, the radiation source array 118 further includes an emitter 404 and a sensor 406 which together may be used to sense reflected radiation that is both (1) of a wavelength different than the radiation from the radiation sources 402 and (2) directed exclusively at the location of a center hole in a blade for supporting a substrate within the chamber.

In addition to cabling 302, the radiation source array 118 may further include a connector 408 adapted to connect to an interface port of the logic 113, thereby making manufacturing and servicing of the apparatus easier.

Turning to FIG. 5, a more detailed exploded perspective view of the lower portion of the base assembly 102 is provided. In addition to providing a means to easily, removeably, and securely couple the apparatus 100 to a processing chamber view port, the base mounting member 114 includes a number of apertures to support both the lower diffuser 116 and the components 402,404,406 of the radiation source array 118. In particular, the apertures include a plurality of approximately normal openings for LEDs or other energy sources and a pair of angled openings for an emitter/sensor pair 404, 406. FIG. 5 depicts the relative positions of the lower diffuser 116, the inner diffuser tube 105, the radiation sources 402, the emitter 404, and the sensor 406, and how each fits into or onto the base mounting member 114. In the example shown, the emitter 404 and the sensor 406 are shown angled at approximately 22.5 degrees to allow optical energy from the emitter 404 to reflect off a substrate on a blade and be received by the sensor 406. However, other practicable angles may be used. Specifically, the emitter 404 and the sensor 406 are preferably angled to lie on lines that intersect at a point on the surface of a substrate supported by a blade within the chamber. A more detailed explanation is provided below with respect to FIG. 10.

Figure 6:
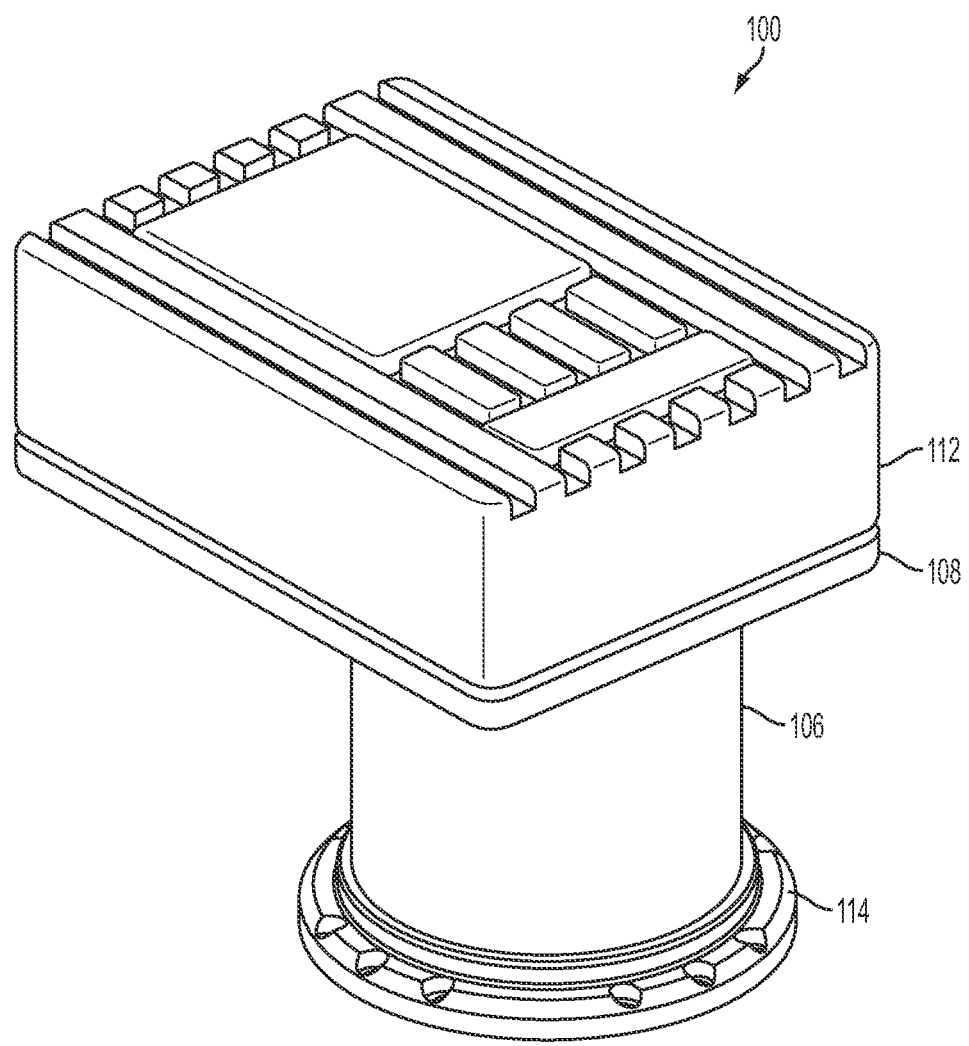
FIG. 6 depicts a front perspective view of the example apparatus embodiment of the present invention.
Figure 7:
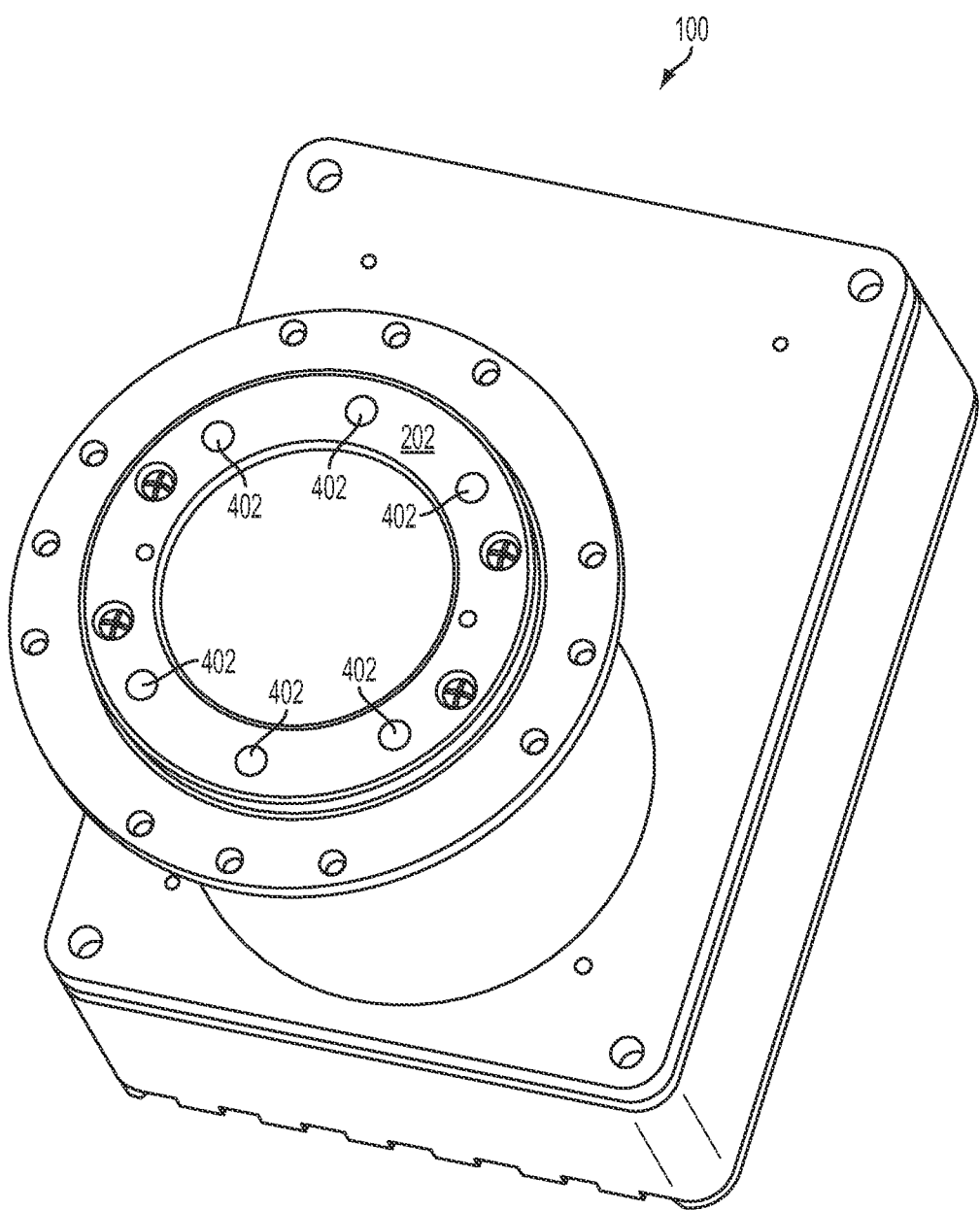
FIG. 7 depicts a bottom perspective view of the example apparatus embodiment of the present invention.

FIGS. 6 and 7 depict front and bottom perspective views, respectively, of the substrate detection apparatus 100. Note that the apparatus 100 may be adapted to have a low profile relative to the lid of a processing chamber to which it is to be mounted. The desired vertical dimension largely defines the inner diffusion tube 105 length and as the length is increased, the amount of diffusion is increased, thereby improving the signal to noise ratio of the apparatus 100. Regarding FIG. 7, note the relative positions of the radiation sources 402 disposed around the lower diffuser 116 to emit an even field of overlapping "field of view" cones onto the substrate. Also note the flat annular surface 202 adapted to sit flush on the view port window of a processing chamber.

Figure 8:
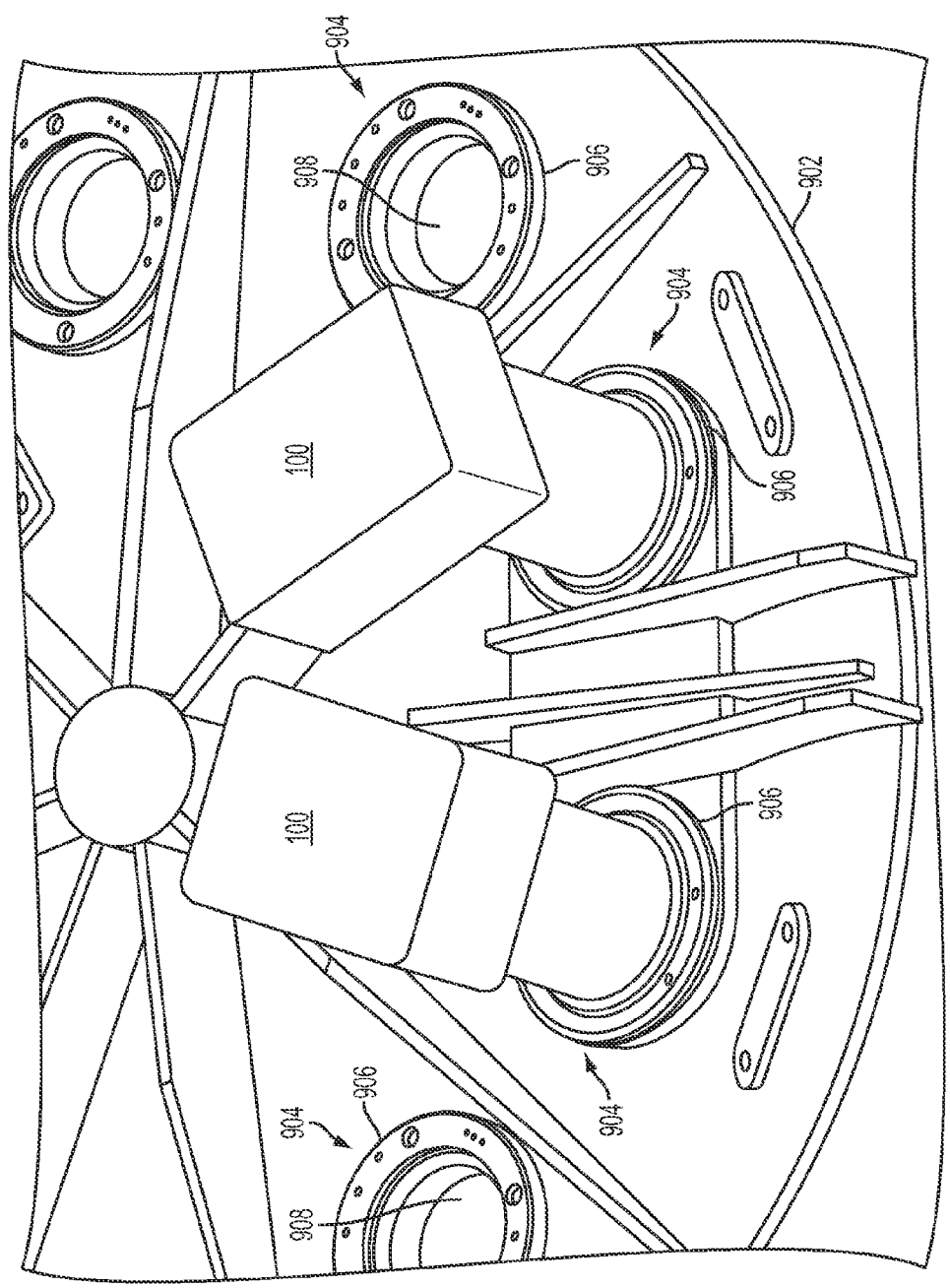
FIG. 8 depicts a perspective view of an example system embodiment of the present invention.

Turning to FIG. 8, a perspective view of an example system embodiment of the present invention is shown. Two substrate detection apparatuses 100 are shown coupled to the lid 902 of a part of a processing tool such as a transfer chamber. The lid 902 includes a plurality of view ports 904 which each include a frame 906 and a transparent window material 908. The apparatuses 100 of the present invention are shown bolted to the frames 906 of two view ports 904 with the flat annular surface 202 (FIG. 7) sitting flush on the transparent window material 908 seated within the frames 906. In the depicted configuration, ambient light is excluded from entering the apparatuses 100 except via the transparent window material 908.

Figure 9:
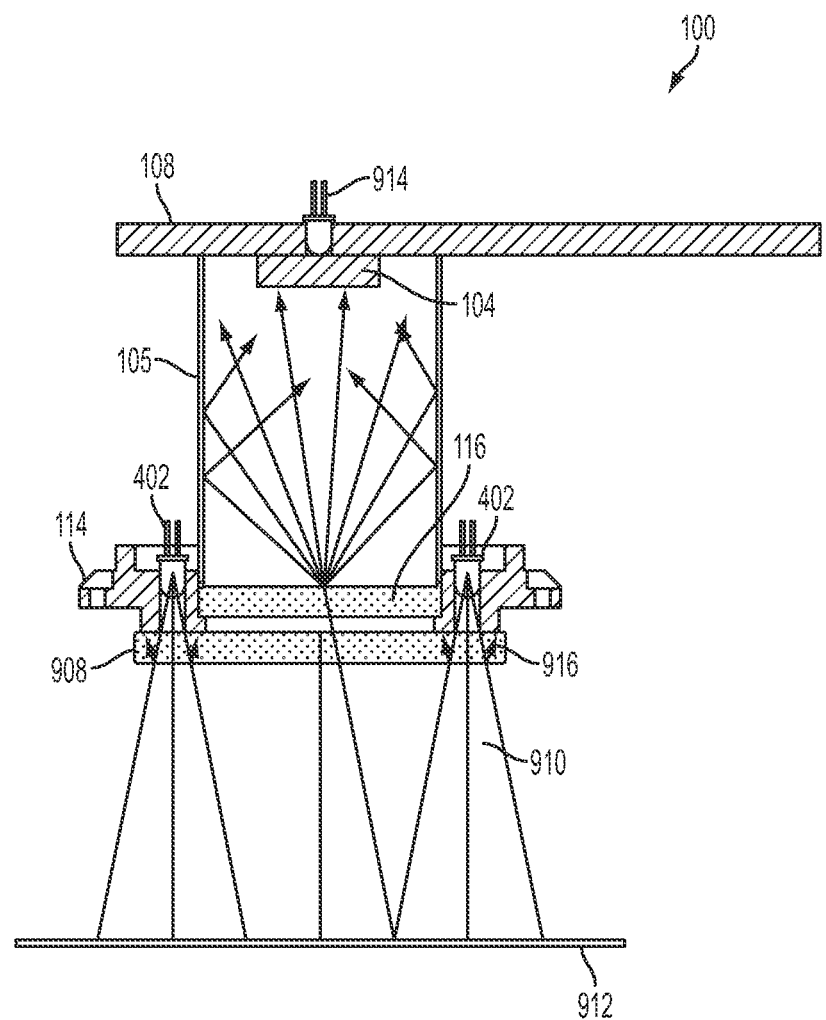
FIG. 9 depicts an example embodiment of the apparatus of the present invention in operation performing a first method of the present invention.
Figure 10:
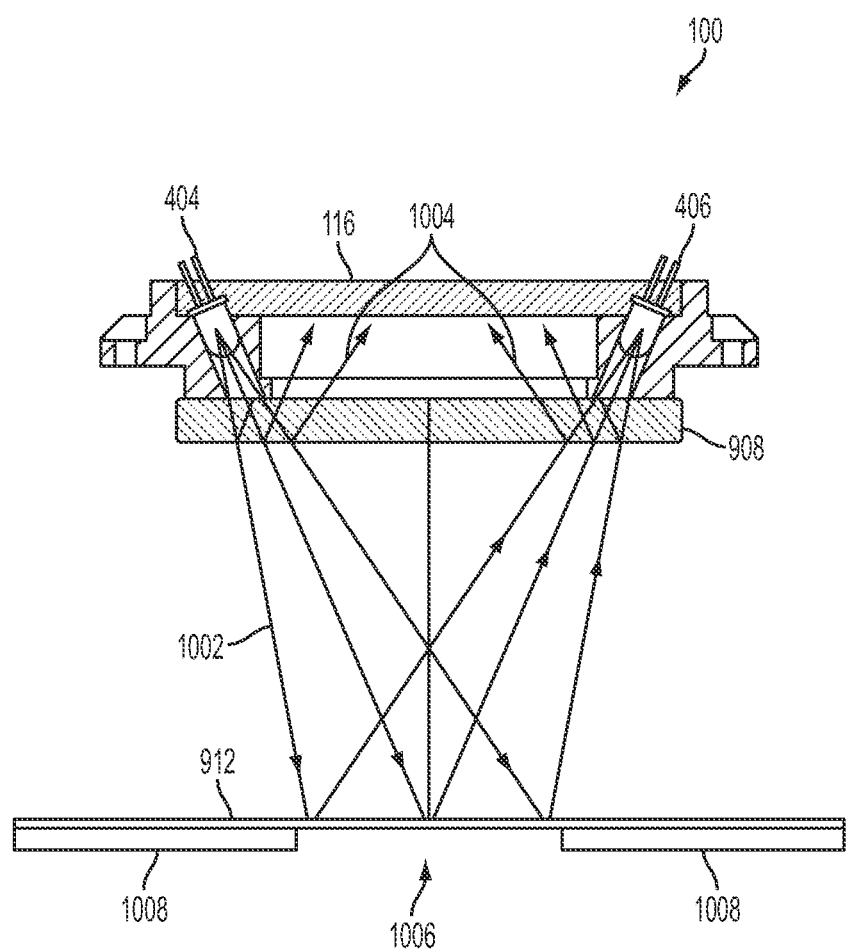
FIG. 10 depicts an example embodiment of the apparatus of the present invention in operation performing a second method of the present invention.

Turning to FIG. 9, a cross-sectional view illustrating a ray trace of the apparatus 100 in operation is provided. The ray trace diagram of FIG. 9 depicts directing radiation of a first wavelength into a chamber and detecting if it is reflected back at a level that is above or below the range an empty blade used to support a substrate would reflect back radiation. In contrast, the ray trace diagram of FIG. 10 depicts directing radiation of a second wavelength into a chamber specifically at a location of a center hole in the blade. While the two methods are shown separately in different diagrams, they may be performed concurrently in parallel to test the two conditions described above for determining if a substrate is present.

As shown in FIG. 9, radiation is emitted from the radiation sources 402 and directed by the apertures in the base mounting member 114 through the transparent window material 908 of the view port 904 of a chamber. As the rays 910 indicate, the radiation may be reflected off a substrate 912 (if present) and/or absorbed by the substrate 912 (if present). Reflected radiation from the substrate 912 may return to the apparatus 100 via the transparent window material 908 and enter the diffusing tube 105 after passing through the lower diffuser 116. The reflected radiation is detected by a sensor 914 of the sensor assembly 110 supported by the plate 108 after passing through the optional upper diffuser 104. Some of the emitted radiation 916 may be reflected by the transparent window material 908 of the view port 904.

As with FIG. 9, the method depicted in FIG. 10 depicts a cross-section of the apparatus 100 and radiation energy rays 1002 emanating from an emitter 404, passing through the transparent window material 908, reflecting off a substrate surface 912, passing back through the transparent window material 908, and being received by a sensor 406. As shown, when a substrate is present, the radiation energy rays 1002 reflect off the substrate surface 912 and the substrate is detected. If the substrate is not present, the rays 102 are not reflected back to the sensor 406, and the apparatus 100 is able to determine that a substrate is not present.

Note that, although not a concern in the depicted method of determining a substrate presence, some rays 1004 are reflected off the transparent window material 908 toward the lower diffuser 116. Thus, different wavelength radiation is preferably used when both the methods depicted in FIGS. 9 and 10 are used concurrently in parallel. Also note that the emitter 404 is angled to cast radiation exclusively on the substrate 912 at a location above the center hole 1006 of the blade 1008 that supports the substrate 912. (Note that the cross-section of the apparatus 100 is taken at line 10,11-10,11 relative to the blade 1008 depicted in FIG. 12 aligned with the center hole 1006 below the center of the base mounting member 114.) Likewise, the sensor 406 is angled to detect radiation reflected from a location on the substrate 912 above the center hole 1006 of the blade 1008 that supports the substrate 912.

Figure 11:
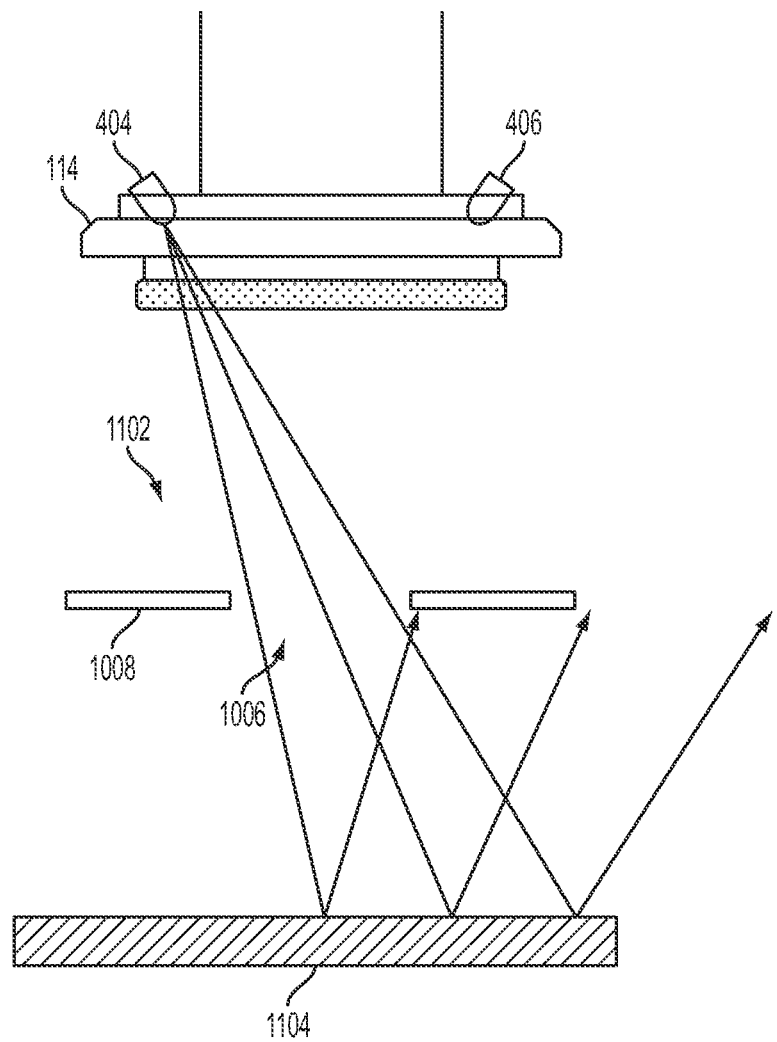
FIG. 11 depicts an example embodiment of the apparatus of the present invention in operation performing a third method of the present invention.
Figure 12:
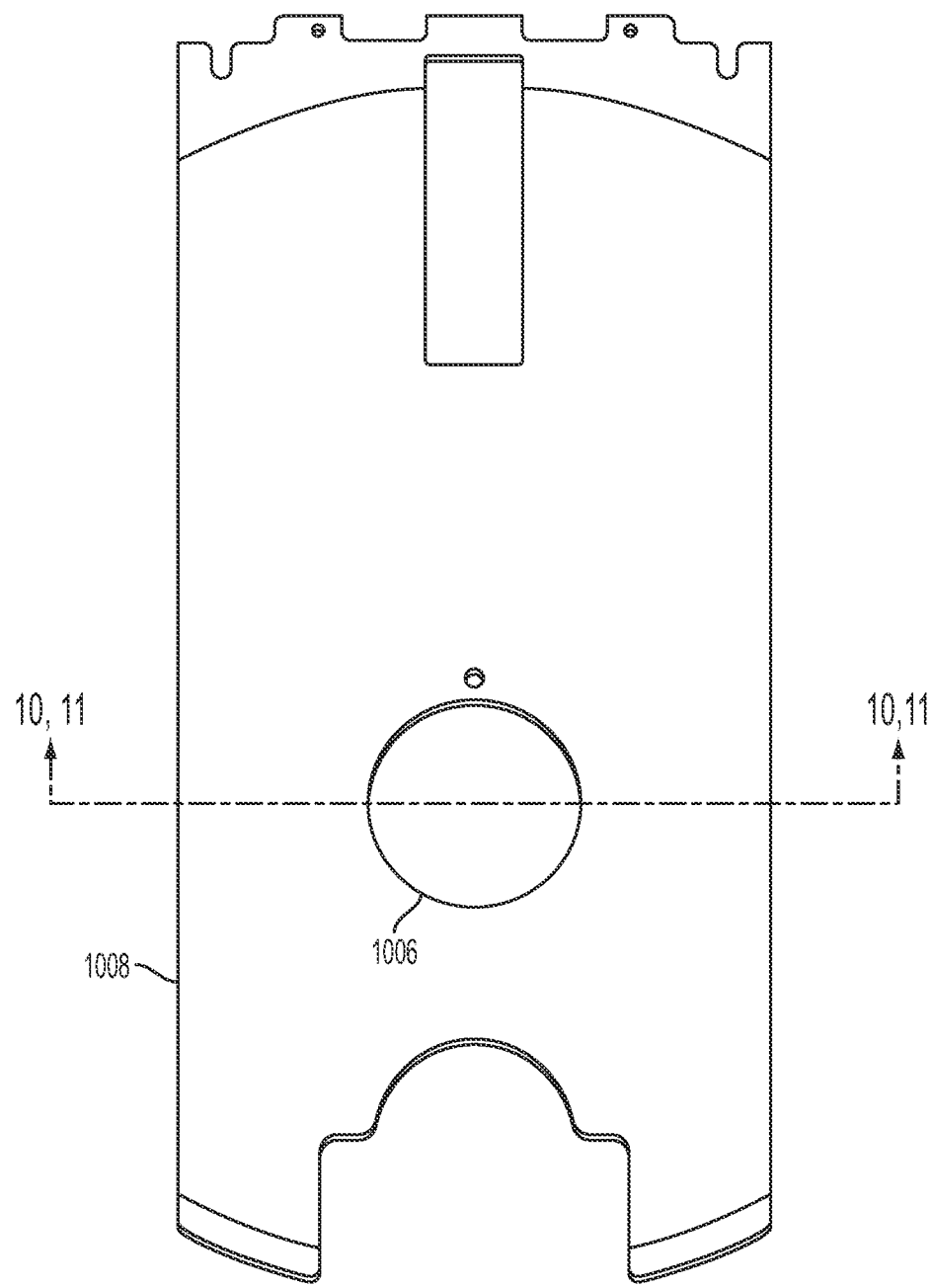
FIG. 12 depicts a blade for supporting a substrate in an electronic device processing chamber.

Turning to FIG. 11, a ray trace diagram is provided that depicts the result when there is no substrate 912 on the blade 1008 and the radiation 1102 is not reflected toward the sensor 406 because it passes through the center hole 1006 in the blade 1008 and reflects off the chamber floor 1104. As indicated above, FIG. 12 depicts an example embodiment of a blade 1008 with a center hole 1006. Numerous alternative blade configurations maybe used with the apparatus 100 of the present invention.

Figure 13:
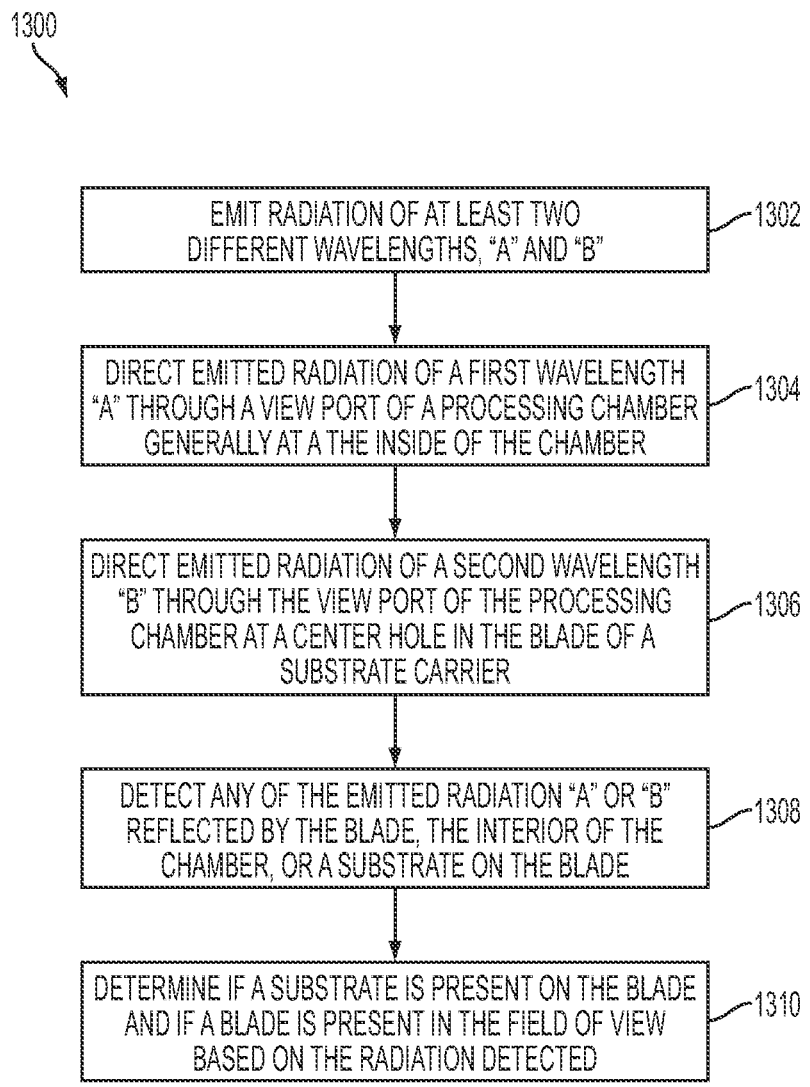
FIG. 13 is a flow chart depicting an example method embodiment of the present invention according to some aspects of the present invention.

FIG. 13 is a flow chart depicting an example method 1300 embodiment of the present invention according to some aspects of the present invention. In Step 1302, radiation of at least two different wavelengths ("A" and "B") are emitted by the radiation sources described above. In Step 1304, radiation of wavelength A is directed through a view port of a processing chamber generally at the inside of the chamber. In Step 1306, radiation of wavelength B is directed through the view port of the processing chamber exclusively at a location of a center hole in the blade of a substrate carrier (e.g., a substrate transfer robot). In Step 1308, the system attempts to detect the radiation of either wavelength that has been reflected by the blade, the interior of the chamber, or a substrate on the blade. In Step 1310, the system determines if a substrate is present on the blade and if a blade is present in the field of view, both based on the reflected radiation detected in Step 1308.

Figure 14:
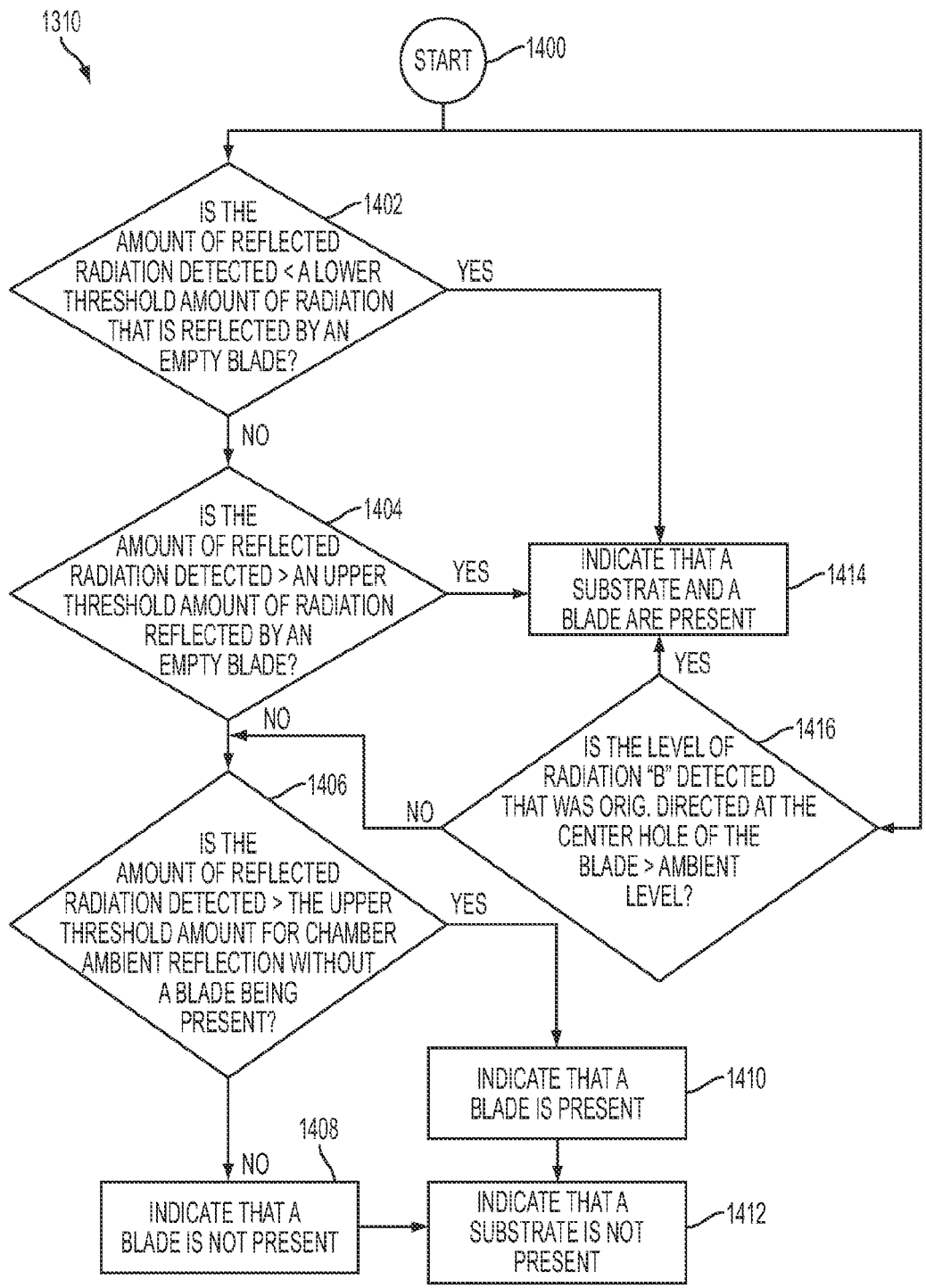
FIG. 14 is a flow chart depicting details of an example embodiment of a portion of the flow chart of FIG. 13 according to some aspects of the present invention.

FIG. 14 is a flow chart depicting details of an example embodiment of Step 1310 of the flow chart of FIG. 13 according to some aspects of the present invention. The example method 1310 begins at Step 1400. The method includes two parallel sub-methods that may be performed by the logic 113 of the apparatus 100 either concurrently or sequentially. The method 1310 depicted in FIG. 14 illustrates concurrent execution of the two sub-methods. From Step 1400, processing flows to Step 1402 and Step 1416. The flow toward Step 1402 will be described first.

In Step 1402, the apparatus 100 determines if the amount of reflected radiation of wavelength A that was detected in Step 1308 (FIG. 13) is less than a lower threshold amount of radiation that would be reflected by an empty blade. In other words, an empty blade is known to reflect an amount of radiation within a range that can be determined, for example, during calibration. If the amount of radiation of wavelength A detected is below the lower bound of this known range, the apparatus may be able to conclude that a substrate is absorbing the radiation. In this case, flow continues to Step 1414 and the apparatus indicates that a substrate and blade are present. Otherwise, flow continues to Step 1404.

In Step 1404, the apparatus 100 determines if the amount of reflected radiation of wavelength A that was detected in Step 1308 (FIG. 13) is greater than an upper threshold amount of radiation that would be reflected by an empty blade. If so, flow continues to Step 1414 and the apparatus indicates that a substrate and blade are present. Otherwise, flow continues to Step 1406.

In Step 1406, the apparatus 100 determines if the amount of reflected radiation of wavelength A that was detected in Step 1308 (FIG. 13) is greater than an upper threshold amount of chamber ambient reflection without a blade being present. If so, flow continues to Step 1410 where the apparatus provides an indication that a blade is present and then to Step 1412 where the apparatus provides an indication that a substrate is not present. Otherwise, flow continues to the Step 1408 where the apparatus provides an indication that a blade is not present and then to Step 1412 where the apparatus provides an indication that a substrate is not present. This completes the first sub-method.

The flow from Step 1400 to Step 1416 is now described. In Step 1416, the apparatus 100 determines if the amount of reflected radiation of wavelength B that was detected in Step 1308 (FIG. 13) that was originally directed at a location of the center hole of the blade, is greater than an ambient level of the wavelength B radiation. If so, flow continues to Step 1414 where the apparatus provides an indication that both a substrate and a blade are present. Otherwise, flow continues to Step 1406.

As above, in Step 1406, the apparatus 100 determines if the amount of reflected radiation of wavelength A that was detected in Step 1308 (FIG. 13) is greater than an upper threshold amount of chamber ambient reflection without a blade being present. If so, flow continues to Step 1410 where the apparatus provides an indication that a blade is present and then to Step 1412 where the apparatus provides an indication that a substrate is not present. Otherwise, flow continues to the Step 1408 where the apparatus provides an indication that a blade is not present and then to Step 1412 where the apparatus provides an indication that a substrate is not present. This completes the second sub-method.

In some embodiments radiation or energy emissions (e.g., emanating from differing locations such as the 402 array and from 404 in FIG. 10) may be of the same wavelength.

In some embodiments, a triple radiation (e.g., three different wavelengths) source application may be used wherein a slightly smaller array 402 including fewer emitters (e.g., four emitters) would be used with second triangulation emitter/sensor pair (e.g., in addition to the first triangulation emitter/sensor pair 404,406). For example, the second triangulation emitter/sensor pair could replace two of the emitters' 402 positions. In some embodiments, six emitters 402 may be used and an additional emitter/sensor pair could be disposed in positions adjacent the six emitters 402. In these configurations, the substrate detection apparatus 100 would include two triangulation sensor functions and a field (bulk) sensor function. In such embodiments, three different wavelengths could be used to prevent interference between the various sensors.

Figure 15:
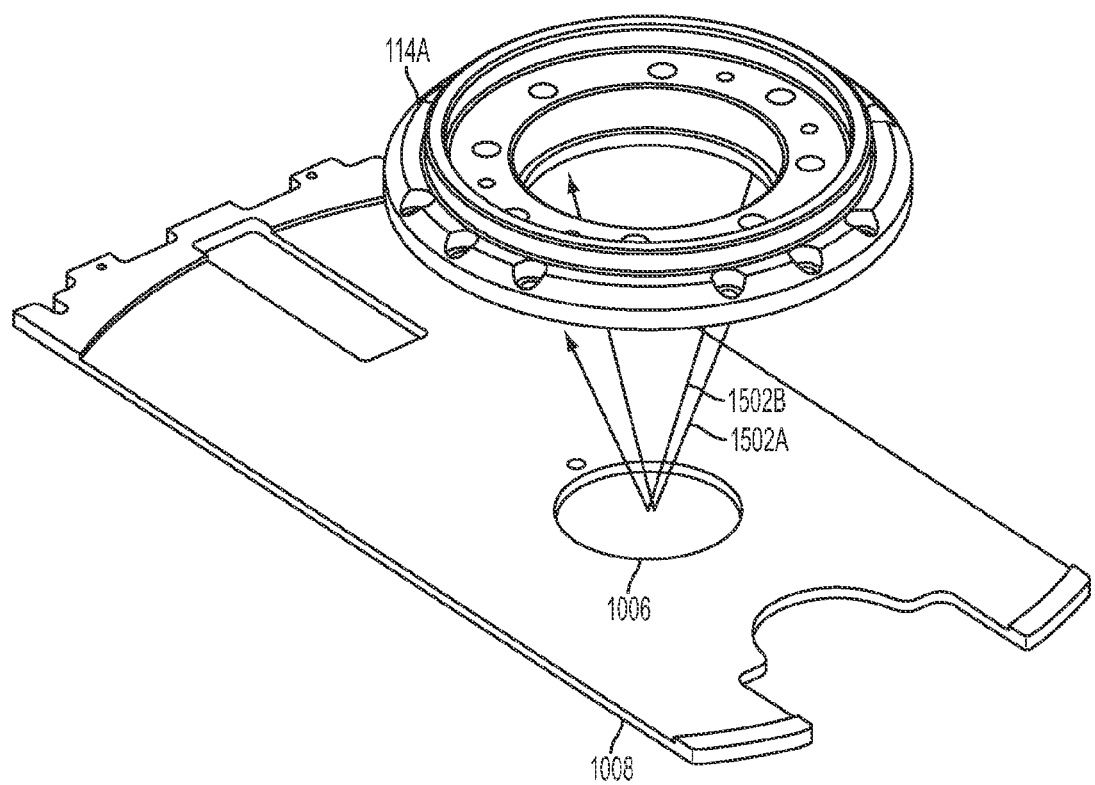
FIGS. 15 and 16 are partial perspective drawings depicting alternative embodiments using three wavelengths of radiation for sensing according to some aspects of the present invention.
Figure 16:
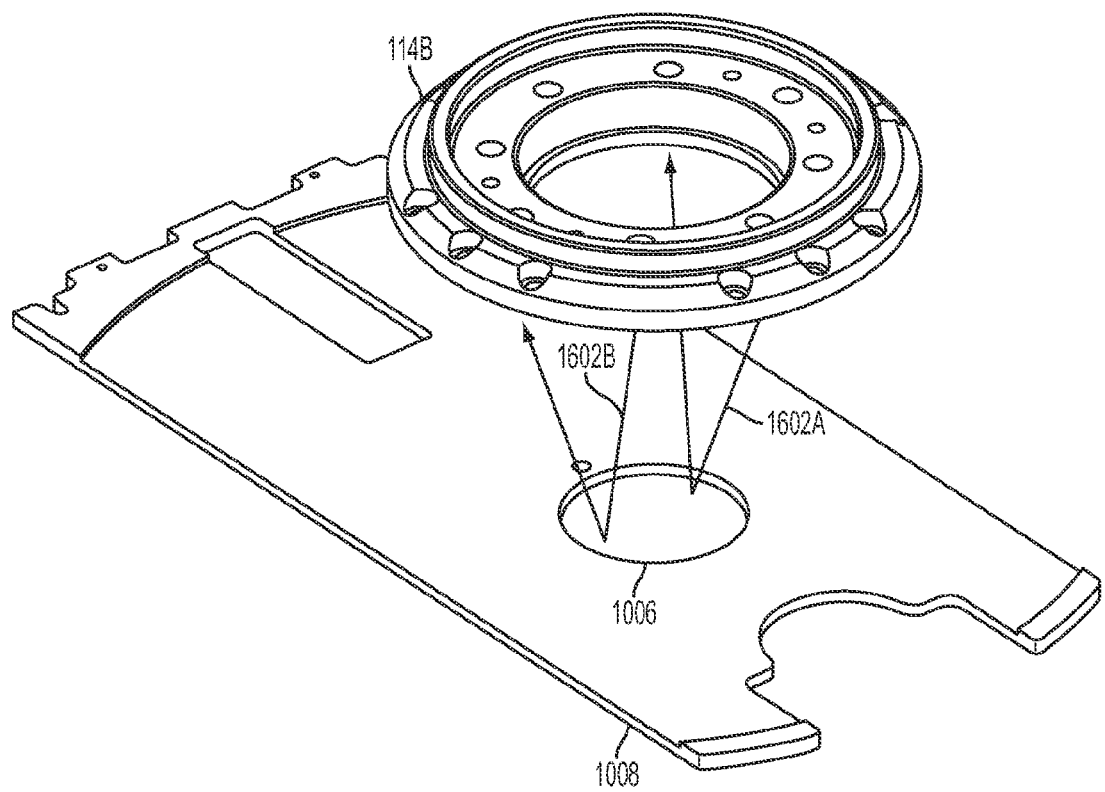

FIGS. 15 and 16 depict embodiments showing applications where there are two different radiation beams converging upon the center hole 1006 in the blade 1008. The remaining LED positions are still used for bulk absorption sensing. Additional positions can be added, and the positions used for the convergent functions can be tilted, grouped together, or otherwise modified to suit.

Three different wavelengths may be used so that the two convergent (reflectivity) sensors do not interfere with one another and also not with the bulk (absorption) sensor. The differing wavelengths may be optimized to sense a wider range of substrate "color" and optical characteristics than two wavelengths may be capable of sensing reliably.

Turning to FIG. 15, an embodiment of a base mounting member 114A that includes apertures for two triangulation emitter/sensor pairs aimed at the location of the hole 1006 in the blade 1008 is shown. Two different beams 1502A, 1502B are shown originating and terminating at approximately orthogonal positions from the base mounting member 114A edge.

Turning to FIG. 16, a second embodiment of a base mounting member 114B that includes apertures for two triangulation emitter/sensor pairs aimed at the location of the hole 1006 in the blade 1008 is shown. Two different beams 1602A, 1602B are depicted whose paths are approximately parallel but aimed at different portions of the central blade hole 1006.

In both embodiments shown in FIGS. 15 and 16, the center opening of the base mounting member 114A remains open for passage of reflected light from the bulk field emitters.

An additional embodiment (not shown) includes three different beam emitter/sensor pairs that all converge upon sensors disposed within the center opening of the base mounting member 114. In such an embodiment, the bulk field sensing function of the other embodiments may not be provided.

In embodiments where the triangulation point of the additional emitter/sensor pair is aimed at the location of the hole 1006 of the blade 1008, the additional emitter/sensor pair could provide a redundant substrate-covering-hole sensing function. Because the additional emitter/sensor pair would be selected for emission and sensitivity at a different wavelength from the others, detection of the substrate could be made more reliable. Extreme variations in the reflectivity of substrates pre- and post-processing have been observed that not only change the reflectivity, but also shift the spectral absorption and reflectance of the substrates. For example, a substrate may go from water clear to light green to deep blue or black depending upon within which stage of processing the substrate is observed.

In some embodiments, the additional emitter/sensor pair may be adapted to triangulate obliquely at the robot wrist which is not normally visible from the view port 904 when looking straight down. In such embodiments, internal prisms or mirrors (e.g., mounted within the chamber) may be used to effect such an optical path. Such embodiments could provide a blade detection function which could be used to turn on the other emitters only when a blade is actually present. This would greatly prolong the useful lifetime of the other emitters.

FIGS. 17A through 19B depict three embodiments of side-looking optics adapted to allow sensing of the robot blade wrist. Note that in the embodiments of FIGS. 17B and 18B, the emitters 404A, 404B are shown in a deeper cutaway than the section cut line for the entire drawing. In many applications, it will not be necessary to modify the blade wrist for reliable detection. However, by providing a chamfered edge at the point where the blade 1008 and wrist meet, the detection reliability may be further enhanced. In particular, if the chamfered edge has an angle approximately perpendicular to the ray paths, more radiation is reflected when the blade is present and detection reliability is even further improved.

In each of the embodiments of the invention described herein, the amount that the center opening of the base mounting member 114 is blocked, is intentionally minimized. In addition, the present invention was conceived and designed to avoid requiring making modification to the interior of the chamber. Doing so would entail actually opening the cover and making modifications such as drilling holes. The debris and potential for leaks that this could cause are to be avoided. In addition, replacing the entire lid with a version having internal mounting holes may not be cost effective.

Looking at FIG. 17B, in some embodiments, the mounting of prisms or mirrors may be accomplished by inclusion of a mounting support ring disposed between the view window 908 and the chamber lid 902. Alignment of the array may be accomplished by means of alignment marks corresponding to features on the window clamp ring mounting surface. However, because the target surface on the blade wrist may itself be curved, the alignment may not be critical.

FIGS. 17A and 17B (perspective and side cross-sectional view respectively) depict a first side-looking embodiment wherein the view port window 908 is modified by bonding or fusing shaped transparent risers 1702 onto the window's 908 lower face. This is maybe done by fusing a tube onto one face of the window 908 and having a closed end section. This allows a fiber optic optical probe (e.g., connected to a spectrometer) to be safely extended well into the process area, sometimes as much as two inches or more.

Advantages of this method include that a more oblique viewpoint can be achieved because the risers can extend as far downward as will safely clear all robot motions. Further, it is an advantage that this method avoids any possible breach of the vacuum seals of the chamber because the standard window may be simply replaced. Further, the shape of the risers 1702 may be modified to achieve any viewing angle desired. In some embodiments, angled surfaces may be coated with a reflective substance depending upon the critical angle between the riser material and vacuum. The vertical surface flats provide clear viewing windows for the optical paths and may be angled to be perpendicular to the ray paths. The emitter and detector may be mounted to the base mounting member 114, safely away from vacuum and thus, presenting no additional path for vacuum leakage over a standard flat window fitment.

While only emission ray traces are shown in FIG. 17B, it should be clear that reflective ray traces can travel along the same paths, or can be triangulated upon a specific point (as in FIG. 17A) by adjustments to the rotation angles of the cut faces of the riser 1702 tips.

In the embodiment shown in FIGS. 17A and 17B, the emitter 404A and detector may be separated and also may optionally be equipped with narrowing apertures so as to limit the viewing area through what are effectively prism mirrors at the riser 1702 tips. The separation of the emitter and detector as shown in FIG. 17A allows for more precise rejection of surface reflections not located at the target point on the blade/robot and also for increased signal to noise ratio due to reduced cross talk there between. In some alternative embodiments, the emitter and detector could also be mounted coaxially through a single riser.

Turning to FIGS. 18A and 18B, the embodiment shown is largely the same as the embodiment of FIGS. 17A and 17B except that the risers 1802 are simpler in manufacture. Shaped prisms or mirrors may be bonded to the ends of the transparent risers 1802, which have themselves been manufactured or bonded to the viewing window 908. Suitable and practicable transparent optical element bonding agents are well-known in the art.

Advantages of the embodiment of FIGS. 18A and 18B over the embodiment of FIGS. 17A and 17B include a number of features. The prisms or mirrors in the embodiment of FIGS. 18A and 18B may be positioned accurately at the time of manufacture without the need to grind or shape the riser pedestals. Further, the angles on the prism or mirror surfaces may be optimized for the desired beam paths more easily than in the embodiment of FIGS. 17A and 17B. In addition, the cost of manufacture of the embodiment of FIGS. 18A and 18B would be substantially less than the cost of manufacture of the embodiment of FIGS. 17A and 17B.

The embodiment of FIGS. 19A and 19B is a variant of the embodiments of FIGS. 17A and 17B and FIGS. 18A and 18B. This embodiment does not have risers, but rather has a prism 1902 or mirror bonded to or manufactured as part of the viewing window 908. An advantage of this embodiment is that a standard viewing window (e.g., a double flat sided window) may be utilized to manufacture the arrangement and only the prism 1902 or mirror would be required to be configured or customized for the beam path.

As in the previous embodiments, the prism 1902 or mirror may be manufactured with sufficient height to lower the viewpoint downward from the position shown. This would have the effect or lowering the ambient reflections from the sides of the circular aperture in the chamber lid 902.

Also as in the previous embodiments, the emitter and detector may be separated or may be coaxial. In the embodiment illustrated in FIG. 19B, an emitter 404A is shown mounted at a small angle from vertical. This optimizes the ray paths into the prism 1902 shown while blocking the main central optical port in the sensor base mounting member 114E as little as possible. In some embodiments, the prism 1902 or mirror may be manufactured as an integral part of the viewing window. In this embodiment, the sensing may be made more reliable by aperture-constricting the emitter and detector so as to limit the reflections from the sides of the circular aperture in the chamber lid 902.

Embodiments of the teachings of the present invention have been described in an illustrative manner. It is to be understood that the terminology, which has been used, is intended to be in the nature of words of description rather than of limitation. Many modifications and variations of the embodiments are possible in light of the above teachings. Therefore, within the scope of the appended claims, the embodiments can be practiced other than as specifically described.

What is claimed is:

1. A method of sensing a substrate in a chamber comprising:
    emitting radiation of at least two different wavelengths;
    directing the emitted radiation of a first wavelength through a view port of a chamber at an interior of the chamber;
    directing the emitted radiation of a second wavelength through the view port of the chamber at a location of a hole in a blade of a substrate carrier;
    detecting any of the emitted radiation reflected by the blade, the interior of the chamber, or a substrate on the blade; and
    determining if a substrate is present on the blade based on the reflected radiation detected.

2. The method of claim 1, wherein determining if a substrate is present includes determining if an amount of the reflected radiation of the first wavelength detected is less than a lower threshold amount of radiation that would be reflected by an empty blade.

3. The method of claim 2, wherein determining if a substrate is present includes determining if an amount of the reflected radiation of the first wavelength detected is greater than an upper threshold amount of radiation that would be reflected by an empty blade.

4. The method of claim 3, wherein determining if a substrate is present includes determining if an amount of the reflected radiation of the second wavelength detected is greater than an ambient level of the radiation of the second wavelength.

5. The method of claim 4 further comprising providing an indication of whether a substrate and a blade are present.

6. The method of claim 4 wherein determining if an amount of the reflected radiation of the second wavelength detected is greater than an ambient level of the radiation of the second wavelength is performed in parallel with determining if an amount of the reflected radiation of the first wavelength detected is less than a lower threshold amount of radiation that would be reflected by an empty blade or greater than an upper threshold amount of radiation that would be reflected by an empty blade.

7. The method of claim 1 further comprising determining if a blade is present in the field of view of a sensor based on the reflected radiation detected.

8. An apparatus for sensing a substrate in a chamber comprising:
    a plurality of emitters for emitting radiation of at least two different wavelengths;
    a member for directing the emitted radiation of a first wavelength through a view port of a chamber at an interior of the chamber;
    one or more apertures in the member for directing the emitted radiation of a second wavelength through the view port of the chamber at a location of a hole in a blade of a substrate carrier;
    one or more sensors for detecting any of the emitted radiation reflected by the blade, the interior of the chamber, or a substrate on the blade; and
    logic coupled to the sensors and adapted to determine if a substrate is present on the blade based on the reflected radiation detected.

9. The apparatus of claim 8, wherein the logic adapted to determine if a substrate is present includes logic adapted to determine if an amount of the reflected radiation of the first wavelength detected is less than a lower threshold amount of radiation that would be reflected by an empty blade.

10. The apparatus of claim 9, wherein the logic adapted to determine if a substrate is present includes logic adapted to determine if an amount of the reflected radiation of the first wavelength detected is greater than an upper threshold amount of radiation that would be reflected by an empty blade.

11. The apparatus of claim 10, wherein the logic adapted to determine if a substrate is present includes logic adapted to determine if an amount of the reflected radiation of the second wavelength detected is greater than an ambient level of the radiation of the second wavelength.

12. The apparatus of claim 11 further comprising logic to generate a signal indicating whether a substrate and a blade are present.

13. The apparatus of claim 11 wherein the logic adapted to determine if an amount of the reflected radiation of the second wavelength detected is greater than an ambient level of the radiation of the second wavelength is adapted to operate in parallel with the logic adapted to determine if an amount of the reflected radiation of the first wavelength detected is less than a lower threshold amount of radiation that would be reflected by an empty blade or greater than an upper threshold amount of radiation that would be reflected by an empty blade.

14. The apparatus of claim 8 further comprising logic adapted to determine if a blade is present in the field of view of a sensor based on the reflected radiation detected.

15. An apparatus for detecting a substrate in an electronic device processing tool comprising:
    a mounting member adapted to couple the apparatus to a view port of the electronic device processing tool;
    a radiation source of a first wavelength disposed within the mounting member and adapted to illuminate an interior of the electronic device processing tool;
    a radiation source of a second wavelength disposed within the mounting member and directed to illuminate a location of a hole in a blade of a substrate carrier in the electronic device processing tool;
    one or more sensors disposed to receive radiation reflected from the substrate, the blade, and the interior of the electronic device processing tool; and
    logic coupled to the sensor and adapted to determine if a substrate is present on the blade based on the reflected radiation received.

16. The apparatus of claim 15 wherein the mounting member includes an aperture disposed to support the radiation source so that only radiation reflected from the substrate, the blade, and the interior of the electronic device processing tool reaches the sensors.

17. The apparatus of claim 15 further including a housing coupled to the mounting member and adapted to exclude radiation from reaching the sensors that is not reflected from the substrate, the blade, and the interior of the electronic device processing tool.

18. The apparatus of claim 17 further including a plurality of diffusers coupled to the housing.

19. The apparatus of claim 18 wherein the plurality of diffusers includes a diffuser disposed at either end of a diffusion tube disposed within the housing.

20. The apparatus of claim 15 further including a diffuser coupled to the mounting member.

* * * * *